United States Patent [19]

Tice et al.

[11] Patent Number: 5,075,109

[45] Date of Patent: Dec. 24, 1991

[54] METHOD OF POTENTIATING AN IMMUNE RESPONSE

[75] Inventors: Thomas R. Tice; Richard M. Gilley; John H. Eldridge; Jay K. Staas; Melinda G. Hollingshead; William M. Shannon, all of Birmingham, Ala.

[73] Assignees: Southern Research Institute; UAB Research Foundation, both of Birmingham, Ala.

[21] Appl. No.: 169,973

[22] Filed: Mar. 18, 1988

Related U.S. Application Data

[63] Continuation-in-part of Ser. No. 923,159, Oct. 24, 1986, abandoned.

[51] Int. Cl.[5] .................. A61K 9/56; A61K 39/085; A61K 39/35; A61K 45/05
[52] U.S. Cl. .................................... 424/88; 424/1.1; 424/89; 424/439; 424/459; 424/461; 424/462; 424/499; 428/402.21; 428/402.24; 514/885; 514/963
[58] Field of Search ............... 428/402.21, 402.24; 424/88, 439, 461, 499, 460, 89, 549; 514/885, 963

[56] References Cited

U.S. PATENT DOCUMENTS

| | | | |
|---|---|---|---|
| 2,738,303 | 3/1956 | Blythe | 424/458 |
| 3,823,228 | 7/1974 | Ferris | 424/494 |
| 4,021,364 | 5/1977 | Speiser et al. | 428/402.22 |
| 4,123,519 | 10/1978 | Tribble et al. | 424/88 |
| 4,152,413 | 5/1979 | Goodnow | 424/494 |
| 4,152,414 | 5/1979 | Harris et al. | 424/490 |
| 4,152,415 | 5/1979 | Harris et al. | 424/494 |
| 4,166,800 | 9/1979 | Fong | 428/402.24 X |
| 4,203,968 | 5/1980 | Harris et al. | 424/92 |
| 4,209,507 | 6/1980 | Ogino et al. | 424/116 |
| 4,269,821 | 5/1981 | Kreuter et al. | 424/489 |
| 4,291,016 | 9/1981 | Nougaret | 424/494 |
| 4,292,298 | 9/1981 | Davis | 424/10 |
| 4,298,002 | 11/1981 | Ronel et al. | 128/260 |
| 4,309,405 | 1/1982 | Guley et al. | 424/493 |
| 4,309,406 | 1/1982 | Guley et al. | 424/489 |
| 4,326,524 | 4/1982 | Drake, Jr. et al. | 128/260 |
| 4,349,530 | 9/1982 | Royer | 424/426 |
| 4,367,217 | 1/1983 | Gruber et al. | 424/494 |
| 4,384,975 | 5/1983 | Fong | 427/213.36 |
| 4,389,330 | 6/1983 | Tice et al. | 264/4.1 X |
| 4,428,925 | 1/1984 | Keith | 424/473 |
| 4,428,926 | 1/1984 | Keith | 424/473 |
| 4,434,153 | 2/1984 | Urquhart et al. | 424/469 |
| 4,439,199 | 3/1984 | Amkraut et al. | 604/894 |
| 4,455,142 | 6/1984 | Martins et al. | 604/890 |
| 4,479,911 | 10/1984 | Fong | 264/4.6 |
| 4,484,923 | 11/1984 | Amkraut et al. | 604/894 |
| 4,524,060 | 6/1985 | Mughal et al. | 424/459 |
| 4,525,339 | 6/1985 | Behl et al. | 424/459 |
| 4,526,938 | 7/1985 | Churchill et al. | 525/405 X |
| 4,530,840 | 7/1985 | Tice et al. | 514/179 |
| 4,542,025 | 9/1985 | Tice et al. | 424/78 |
| 4,559,303 | 12/1985 | Aotani et al. | 435/180 |
| 4,585,651 | 4/1986 | Beck et al. | 424/88 |
| 4,590,170 | 5/1986 | Akiyoshi et al. | 436/533 |
| 4,610,870 | 9/1986 | Jain et al. | 424/465 |
| 4,613,500 | 9/1986 | Suzuki et al. | 424/85 |
| 4,650,769 | 3/1987 | Kakimi et al. | 436/533 |
| 4,681,752 | 7/1987 | Melillo | 424/91 X |
| 4,690,682 | 9/1987 | Lim | 604/891 |
| 4,732,763 | 3/1988 | Beck et al. | 424/433 |
| 4,764,359 | 8/1988 | Lemelson | 424/85 X |
| 4,783,336 | 11/1988 | Margel et al. | 424/462 |
| 4,925,673 | 5/1990 | Steiner et al. | 424/455 |

FOREIGN PATENT DOCUMENTS

| | | |
|---|---|---|
| 523028 | 10/1979 | Australia . |
| 526326 | 7/1980 | Australia . |
| 3108884 | 1/1985 | Australia . |
| 0126537 | 11/1984 | European Pat. Off. . |
| 0130162 | 1/1985 | European Pat. Off. . |
| 0126537 | 3/1987 | European Pat. Off. . |
| 2287216 | 5/1976 | France ........................ 424/461 |
| 8706129 | 10/1987 | PCT Int'l Appl. . |
| 8801213 | 2/1988 | PCT Int'l Appl. . |
| 8809163 | 12/1988 | PCT Int'l Appl. . |
| 2160312 | 12/1985 | United Kingdom . |

OTHER PUBLICATIONS

Ostro, *Scientific American*, Jan. 1987, 102-111.
DeLuca et al., "Porous Biodegradable Microspheres for Parenteral Administration" in Tropics in Pharmaceutical Sciences 1987, Elsevier Science Publishers, B.V., Amsterdam, pp. 429-442.
Artursson et al., *Journal of Pharmaceutical Science*, 73:1507, 1984.
Chang, *Journal of Bioengineering*, 1:25, 1976.
O'Hagen, Palin & Davis, *Critical Reviews in Therapeutic Drug Carrier Systems*, 4:197, 1978.
Read, et al., *Critical Reviews in Therapeutic Drug Carrier Systems*, 4:221, 1987.
Harmsen et al., *Science*, 230:1277, 1985.
Klipstein et al., *Infection and Immunity*, 39:1000, 1983.
Margel et al., *J. Cell. Sci.*, 56:157, 1982.
Hay et al., *Proc. Soc. Exp. Biol. Med.*, 150:641, 1975.
Juliano et al., *Biochem. Biophys. Res. Commun.*, 63:651. 1975.

*Primary Examiner*—Richard D. Lovering
*Attorney, Agent, or Firm*—Needle & Rosenberg

[57] ABSTRACT

A method of delivering a bioactive agent to an animal entailing the steps of encapsulating effective amounts of the agent in a biocompatible excipient to form microcapsules having a size ranging from between approximately one micrometer to approximately ten micrometers and admnistering effective amounts of the microcapsules to the animal. A pulsatile response is obtained, as well as mucosal and systemic immuity. Related compositions are also provided.

2 Claims, No Drawings

METHOD OF POTENTIATING AN IMMUNE RESPONSE REFERENCE TO CO-PENDING APPLICATION

This application is a continuation-in-part of applicant's co-pending Ser. No. 923,159, filed Oct. 24, 1986.

BACKGROUND OF THE INVENTION

This invention relates to a method and a formulation for orally administering a bioactive agent encapsulated in one or more biocompatible polymer or copolymer excipients, preferably a biodegradable polymer or copolymer, affording microcapsules which due to the proper size of the resultant microcapsules results in the agent reaching and being taken up by the folliculi lymphatic aggregati, otherwise known as the "Peyer's patch," or "GALT" of the animal without loss of effectiveness due to the agent having passed through the gastrointestinal tract. Similar folliculi lymphatic aggregati can be found in the bronchei tubes (BALT) and the large intestine. Hereafter, the above-described tissues are referred to in general as mucosally associated lymphoreticular tissues.

The use of microencapsulation to protect sensitive bioactive agents from degradation has become well-known. Typically, a bioactive agent is encapsulated within a protective wall material, usually polymeric in nature. The agent to be encapsulated can be coated with a single wall of polymeric material (microcapsules), or can be homogeneously dispersed within a polymeric matrix (microspheres). (Hereafter, the term microcapsules refers to both microcapsules and microspheres). The amount of agent inside the microcapsule can be varied as desired, ranging from either a small amount to as high as 95% of the microcapsule composition. The diameter of the microcapsule can also be varied as desired, ranging from less than one micrometer to as large as three millimeters or more.

Peyer's patches are conglomerations of lymphoid nodules located in the illeum or lower part of the intestine, and are an important part of the body's defense against bacterial infection. Antigens are substances that promote antibody formation, and include such things as foreign protein or tissue. All antibodies belong to a class of proteins call immunoglobulins (Ig). When an antibody and antigen combine, they form an inactive complex, thus neutralizing the antigen.

Peyer's patches possess IgA precursor B cells which can populate the lamina propria regions of the gastrointestinal and upper respiratory tracts and differentiate into mature IgA synthesizing plasma cells. It is these plasma cells which actually secrete the antibody molecules. Studies by Heremans and Bazin measuring the development of IgA responses in mice orally immunized with antigen showed that a sequential appearance of antigen-specific IgA plasma cells occurred, first in mesenteric lymph nodes, later in the spleen, and finally in the lamina propria of the gastrointestinal tract (Bazin, H., Levi, G., and Doria, G. Predominant contribution of IgA antibody-forming cells to an immune response detected in extraintestinal lymphoid tissues of germfree mice exposed to antigen via the oral route. J. Immunol. 105: 1049; 1970 and Crabbe, P. A., Nash, D. R., Bazin, H. Eyssen, H., and Heremans, J. F. Antibodies of the IgA type in intestinal plasma cells of germfree mice after oral or parenteral immunization with ferritin. J. Exp. Med. 130: 723; 1969) It is apparent, therefore, that Peyer's patches are enriched sources of precursor IgA cells, which, subsequent to antigen sensitization, follow a circular migrational pathway and account for the expression of IgA at distant mucosal surfaces. This circular pattern provides a common mucosal immune system by continually transporting sensitized B cells to mucosal sites for responses to gut-encountered environmental antigens and potential pathogens.

Of particular importance to the present invention is th ability of oral immunization to induce protective antibodies. It is known that the ingestion of antigens by animals results in the appearance of antigen-specific secretory IgA antibodies in bronchial or nasal washings. For example, studies with human volunteers show that oral administration of influenza vaccine is effective at inducing secretory anti-influenza antibodies in nasal secretions.

It is apparent that any method or formulation involving oral administration of an ingredient be of such design that will protect the agent from degradation during its passage through the gastrointestinal tract. If not, the ingredient will reach the Peyer's patch, if at all, in an inadequate quantity or ineffective condition. In unprotected form large quantities of the bioactive agent must be taken for an effective amount of the agent to reach the Peyer's patch. The result is that a large percentage of the administered agent is unused. Also, frequent oral administrations are necessary to achieve a prolonged delivery of agent to the Peyer's patch. Such frequent administration of high doses of agent is both wasteful and inconvenient.

Therefore, there exists a need for a method of oral immunization which will effectively stimulate the mucosal immune system and overcome the problem of degradation of the bioactive ingredient during its passage through the gastrointestinal tract to the Peyer's patch. There exists a more particular need for a method of targeting an antigen to the Peyer's patch and releasing that antigen once in the Peyer's patches.

SUMMARY OF THE INVENTION

This invention relates to a method and formulation for targeting to and then releasing a bioactive agent in the Peyer's patch of an animal by oral administration. The agent is microencapsulated in a biocompatible polymer or copolymer, preferably a biodegradable polymer or copolymer which is capable of passing through the gastrointestinal tract without degradation or minimal degradation so that the agent reaches the Peyer's patch unaltered and in effective amounts. The term biocompatible is defined as a polymeric material which is not toxic to the body, is not carcinogenic, and should not induce inflammation in body tissues. It is preferred that the microcapsule polymeric excipient be biodegradable in the sense that it should degrade by bodily processes to products readily disposable by the body and should not accumulate in the body. The microcapsulate is also of a size capable of being selectively taken up by the selective Peyer's patch. Therefore, the problems of the agent reaching the Peyer's patch and being taken up are solved.

Further, this invention relates to a method of potentiating an immune response by parenterally administering, such as by injection, an effective amount of at least two populations of bioactive-agent containing biocompatible microcapsules such that one of the microcapsule populations is sized between approximately 1-10 μm. This procedure provides for one-shot administration of antigen or allergen that is released in a pulsed manner to potentiate both a primary immunological response and subsequent immunological response.

It is an objective of this invention to provide a method of orally administering a bioactive ingredient to an animal which results in the ingredient reaching and being taken up by the Peyer's patch, and thereby stimulating the mucosal immune system, without losing its effectiveness as a result of passing through the animal's gastrointestinal tract.

It is a still further objective of this invention to provide a formulation consisting of a core bioactive ingredient and an encapsulating polymer or copolymer excipient which is biocompatible and, preferably biodegradable as well, which can be utilized in the oral-administration methods described above.

It is another object of this invention to provide an improved vaccine delivery system which obviates the need for immunopotentiators.

It is a still further objective of this invention to provide an improved vaccine delivery system for the induction of immunity as pulsatile responses obtained from a single administration of microencapsulated antigen.

It is a still further objective of this invention to provide an improved vaccine delivery system which both obviates the need for immunopotentiators and affords induction of immunity as pulsatile responses all from a single administration of microcapsulated antigen.

DETAILED DESCRIPTION OF THE INVENTION

An illustration of the method of performing one embodiment of the invention, that is, the Peyer's patch targeting and prolonged delivery of the antigens trinitrophenyl keyhole limpet hemocyanin and staphylococcal enterotoxin B encapsulated in 50:50 poly(DL-lactide-co-glycolide) to mice follows:

It should be noted, however, that other polymers besides poly(DL-lactide-co-glycolide) may be used. Examples of such polymers include, but are not limited to, poly(glycolide), poly(DL-lactide-co-glycolide), copolyoxalates, polycaprolactone, poly(lactide-co-caprolactone), poly(esteramides), polyorthoesters and poly(8-hydroxybutyric acid), and polyanhydrides.

Also, other bioactive ingredients may be used. As used herein, the terms "bioactive agent" or "bioactive ingredient" refer to therapeutic or preventative agents to improve the health of animals, such as antigens, allergens, and drugs. Example of such include, but are not limited to, antigens to vaccinate against viral, bacterial, protozoan, fungal diseases such as influenza, respiratory syncytial, parainfluenza viruses, *Hemophilus influenzae, Bordetella pertussis, Neisseria gonorrhoeae, Streptococcus pneumoniae* and *Plasmodium falciparum* or other diseases caused by pathogenic microorganisms or antigens to vaccinate against diseases caused by macroorganisms such as helminthic pathogens or antigens to vaccinate agains allergies or pharmaceutical drugs such as etretinate, peptides, proteins, nucleic acids and the like.

I. MICROENCAPSULATION

A. Preparation of Dye-Loaded Microcapsules for Peyer's-Patches

Penetration Studies

Coumarin, a water-insoluble dye was microencapsulated with polystyrene, a nonbiodegradable polymer, to afford colorful microcapsules that could be used to follow the penetration of microcapsules into the Peyer's patches. The procedure used to prepare these microcapsules follows: First, a polymer solution is prepared by dissolving 4.95 g of polystyrene (Type 685D, Dow Chemical Company, Midland, Mich.) in 29.5 g of methylene chloride (Reagent Grade, Eastman Kodak, Rochester, N.Y.). Next, about 0.05 g of coumarin (Polysciences, Inc., Warrington, Pa.) is added to the polymer solution and allowed to dissolve by stirring the mixture with a magnetic stir bar.

In a separate container, 10 wt % aqueous poly(vinyl alcohol) (PVA) solution, the processing medium is prepared by dissolving 40 g of PVA (Vinol 2050, Air Products and Chemicals, Allentown, Pa.) in 360 g of deionized water. After preparing the PVA solution, the solution is saturated with methylene chloride b adding 6 g of methylene chloride. Next, the PVA solution is adde to a 1-L resin kettle (Ace Glass, Inc., Vineland, N.J.) fitted with a truebore stir shaft and a 2.5-in. TEFLON impeller and stirred a about 380 rpm by a Fisher stedi speed motor.

The polystyrene/coumarin mixture is then added to the resin kettle containing the PVA processing media. This is accomplished by pouring the polystyrene/coumarin mixture throu long-stem 7-mm bore funnel which directs the mixture into the resin kettle. A stable oil-in-water emulsion results and is subsequently stirred for about 30 min. at ambient pressure to afford oil microdroplets of the appropriate size. Then the resin kettle is closed, and the pressure in the resin kettle is gradually reduced to 520 mm Hg by means of a water aspirator connected to a manometer and a bleed valve. The resin kettle contents are stirred at reduced pressure for about 24 h to allow all of the methylene chloride to evaporate. After all of the methylene chloride has evaporated, the hardened microcapsules are collected by centrifugation and dried for 72 h in a vacuum chamber maintained at room temperature.

B. Preparation of Antigen-Loaded Microcapsules

TNP-KLH, a water-soluble antigen, was encapsulated in poly(DL-lactide-co-glycolide), a biocompatible, biodegradable polyester. The procedure used to prepare the microcapsules follows:

First, a polymer solution was prepared by dissolving 0.5 g of 50:50 poly(DL-lactide-co-glycolide) in 4.0 g of methylen chloride. Next, 300 microliter of an aqueous solution of TNP-KLH (46 mg TNP-LKH/mL; after dialysis) was added to and homogeneously dispersed in the poly(DL-lactide-co-glycolide) solution by vortexing the mixture with a Vortex-Genie 2 (Scientific Industries, Inc., Bohemia, N.Y.).

In a separate container, a 8 wt % aqueous PVA solution was prepared by dissolving 4.8 g of PVA in 55.2 g of deionized water. After dissolution of the PVA, the PVA solution was added to a 100-mL resin kettle (Kontes Glass, Inc., Vineland, N.J.) fitted with a truebore stirrer and a 1.5-in TEFLON turbine impeller. The polymer solution was then added to the PVA processing medium by pouring through a long-stem 7-mm bore funnel. During this addition, the PVA solution was being stirred at about 650 rpm. After the resulting oil-in-water emulsion was stirred in the resin kettle for about 10 min, the contents of the resin kettle were transferred to 3.5 L of deionized water contained in a 4-L beaker and being stirred at about 800 rpm with a 2-in. stainless steel impeller. The resultant microcapsules were stirred in the deionized water for about 30 min, collected by centrifugation, washed twice with deionized water to remove any residual PVA, and were then collected by freeze drying. The microcapsule products consisted of spherical particles about 1 to 10 micrometer in diameter. (Note: staphylococcal enterotoxin B microcapsules can be made in a similar manner.)

The TNP-KLH content of the antigen-loaded microcapsules that is, the core loading of the microcapsules, was determined by weighing out 10 mg of antigen-loaded microcapsules in a 12-mL centrifuge tube. Add 3.0 mL of methylene chloride to the tube an vortex to dissolve the poly(DL-lactide-coglycolide). Next, add 3.0 mL of deionized water to the tube and vortex vigorously for 1 min. Centrifuge the contents of the centrifuge tube to separate the organic and aqueous layers. Transfer the aqueous layer to a 10-mL volumetric flask. Repeat the extraction combining the aqueous layers in the volumetric flask. Fill the flask to the mark with deionized water. The amount of TNP-KLH in the flask and subsquently, the amount of TNP-KLH in the microcapsules is then quantified using a protein assay. The microcapsules contained 0.2% TNP-KLH by weight. (Note: The staphylococcal enterotoxin B content of staphylococcal enterotoxin B microcapsules can be quantiifed in a similar manner.)

II. BIOLOGICAL STUDY ONE

A. Mice

BALB/c mice, 8 to 12 weeks of age, were used in these studies.

B. Trinitrophenyl—Keyhole Limpet Hemocyanin

Hemocyanin from the keyhole limpet (KLH) Megathura crenulate was purchased from Calbiochem (San Diego, Calif.). It was conjugated with the trinitrophenyl hapten (TNP-KLH) using 2, 4, 6-trinitrobenzene sulfonic acid according to the procedure of Rittenburg and Amkraut (Rittenburg, M. B. and Amkraut, A. A. Immunogenicity of trinitrophenyl-hemocyanin: Production of primary and secondary anti-hapten precipitins. J. Immunol. 97: 421; 1966). The substitution ratio was spectrophotometrically determined to be $TNP_{861}$-KLH using a molar extinction coefficient of 15,400 at a wavelength of 350 nm and applying a 30% correction for the contribution of KLH at this wavelength (Rittenburg, M. B. and Amkraut, A. A. Immunogenicity of trinitrophenyl-hemocyanin: Production of primary and secondary anti-hapten precipitins. J. Immunol. 97: 421; 1966).

C. Immunization

Microencapsulated and nonencapsulated TNP-KLH was suspended at an antigen concentration of 10 microgram/mL in a solution of 8 parts filter sterilized tap water and 2 parts sodium bicarbonate (7.5% solution). The recipient mice were fasted overnight prior to the administration of 0.5 mL of suspension via gastric intubation carried out with an intubation needle (Babb, J. L. Kiyono, H., Michalek, S. M. and McGhee, J. R. LPS regulation of the immune response: Suppression of immune responses to orally-administered T-dependent antigen. J. Immunol. 127: 1052; 1981).

D. Collection of Biological Fluids

1. Serum

Blood was collected in calibrated capillary pipettes following puncture of the retro-orbital plexus. Following clot formation, the serum was collected, centrifuged to remove red cells and platelates, heat-inactivated, and stored at $-70°$ C. until assayed.

2. Intestinal secretions

Mice were administered four doses (0.5 mL) of lavage solution (25 mM NaCl, 40 mM $Na_2SO_4$, 10 mM KCl, 20 mM $NaHCO_3$, and 48.5 mM poly(ethylene glycol), osmolarity of 530 mosM) at 15-min intervals (Elson, C. O. Ealding, W. and Lefkowitz, J. A lavage technique allowing repeated measurement of IgA antibody on mouse intestinal secretions. J. Immunol. Meth. 67: 101; 1984). Fifteen minutes after the last dose of lavage solution, the mice were anesthetized and after an additional 15 min they were administered 0.1 mg pilocarpine by ip injection. Over the next 1 to 20 min a discharge of intestinal contents was stimulated Thi was collected into a petri dish containing 3 mL of a solution of 0.1 mg/mL soybean trypsin inhibitor (Sigma, St. Louis, Mo.) in 50 mM EDTA, vortexed vigorously and centrifuged to remove suspended matter. The supernatant was transferred to a round-bottom, polycarbonate centrifuge tube and 30 micrograms of phenylmethylsulfonyl fluoride (PMSF, Sigma) was added prior to clarification by high-speed centrifugation (27,000 x g, 20 min, $4°$ C). After clarification, 20 micrograms each of PMSF and 1% sodium azide were added and the solution made 10% in FCS to provide an alternate substrate for any remaining proteases.

3. Saliva

Concurrent with the intestinal discharge, a large volum of saliva is secreted and 0.25 mL was collected into a pasteur pipette by capillary action. Twenty microliters each of soybean trypsin inhibitor, PMSF, sodium azide and FCS was added prior to clarification.

E. Immunochemical Reagents

Solid-phase absorbed and affinity-purified polyclonal goat IgG antibodies specific for murine IgM, IgG and IgA were obtained commercially (Southern Biotechnology Associates, Birmingham, Ala.). Their specificity in radioimmunoassays were tested through their ability to bind appropriate monoclonal antibodies and myeloma proteins

F. Solid-Phase Radioimmunoassays

Purified antibodies were labeled with carrier-free $Na^{125}I$ (Amersham) using the chloramine T method (Hunter, W. M. Radioimmunoassay. In: Handbook of Experimental Immunolog M. Weir (editor). Blackwell Scientific Publishing, Oxford. p. 14.1; 1978). Immulon Removawell assay strips (Dynatech) were coated with TNP conjugated bovine serum albumin (BSA) at 1 microgram/mL in BBS overnight at $4°$ C. Control strips were left uncoated but all strips were blocked for 2 h at room temperature with 1% BSA in BBS, which was used as the diluent for all samples and $^{125}I$-labelled reagents. Samples of biologic fluids were diluted to contain 1 to 1,000 ng/mL of antigen-specific antibody of the isotype under study, added to washed triplicate replicate wells, and incubated 6 h at room temperature. After washing, 100,000 cpm of $^{125}I$-labelled isotype-specific anti-immunoglobulin was added to each well and incubated overnight at 4 degrees Centigrade. Following the removal of unbound $^{125}I$-antibodies by washing, the wells were counted in a Gamma 5500 spectrometer (Beckman Instruments, Inc., San Ramon, Calif.). Calibrations were made using serial twofold dilutions of a standard serum (Miles Scientific, Naperville, Ill.) containing known amounts of immunoglobulins, on wells coated with 1 microgram/well isotype-specific antibodies. Calibration curves and interpolation of unknowns was obtained by computer, using "Logit-log" or "Four Parameter Logistic" BASIC Technology Center (Vanderbilt Medical Center, Nashville, Tenn.).

G. Results

1. Penetration of dye-loaded microcapsules into the Peyer's patches

The uptake of microcapsules into the gut-associated lymphoreticular tissues and the size restriction of this penetration was investigated by orally administering to mice polystyrene microcapsules, loaded with the fluorescent dye coumarin. Unanesthetized, fasted BALB/c mice were administered 0.5 mL of a 100 mg/mL suspension of various sized fluorescent microcapsules (less than 5 micrometers or 8 to 50 micrometers in diameter) in tap water into the stomach using a feeding needle. At various time after administration (0.5, 1 and 2 h), the mice were sacrificed and the small intestine excised. One-centimeter sections of gut containing a discrete Peyer's patch were isolated flushed of lumenal contents, everted, and snap frozen.

Frozen sections were prepared and examined under a fluorescence microscope to observe the number, location and size of the microcapsules which were taken up into the Peyer's patch from the gut lumen.

Although some trapping of the microcapsules between the villi had prevented their removal during flushing, no penetration into the tissues was observed at any point except the Peyer's patch. At 0.5 h after oral administration, microcapsules were observed in the Peyer's patch of the proximal, but not the distal, portion of the small intestine. With increasing time the microcapsules were transported by peristaltic movement such that by 2 h they were throughout the gastrointestinal tract and could be found in the Peyer's patch of the illeum. The endocytosed microcapsules were predominantly located peripherally, away from the apex of the Peyer's patch dome, giving the impression that physical trapping between the dome and adjacent villi during peristalsis had aided in their uptake. Although some particles u to 10 micrometers in diameter were observed within the Peyer's patch, microcapsules of less than 5 micrometers in diameter were taken up in greater numbers and were observed to progress deeper into the Peyer's patch over the time period examined These results demonstrate that microcapsules of 1 to 5 micrometers in diameter are rapidly and selectively taken up from the gut lumen into the Peyer's patch. This suggested that microcapsules composed of biodegradable wall materials would serve as an effective means for the targeted delivery of antigens to the lymphoreticular tissues for the induction of immunity at mucosal surfaces.

2. Oral Immunization With Antigen-Loaded Biodegradable Microcapsules

Microcapsules containing the haptenated protein antigen trinitrophenyl-keyhold limpet hemocyanin (TNP-KLH) were prepared using poly(DL-lactide-co-glycolide) copolymers as wall materials These microcapsules were separated according to size and those in the range of 1 to 5 micrometers in diameter were selected for evaluation. These microcapsules contained 0.2% antigen by weight Their ability to serve as an effective antigen delivery system when ingested was tested by administering 0.5 mL of a 10 mg/mL suspension (10 micrograms antigen) in bicarbonate-buffered sterile tap water via gastric intubation on 4 consecutive days. For comparative purposes an additional group of mice was orally immunized in parallel with 0.5 mL of 20-micrograms/mL solution of unencapsulated TNP-KLH Control mice were orally administered diluent only.

On Days 14 and 28 following the final immunization, serum, saliva and gut secretions were obtained from 5 fasted mice in each group. These samples were tested in isotype-specific radioimmunoassays to determine the levels of TNP-specific and total antibodies of the IgM, IgG and IgA isotypes (Table 1). The samples of saliva and gut secretions contained antibodies which were almost exclusively of the IgA class. These results are consistent with previous studies and provide evidence that the procedures employed to collect these secretions do not result in contamination with serum. None of the immunization protocols resulted in significant changes in the total levels of immunoglobulins present in any of the fluids tested. Low but detectable levels of naturally-occurring anti-TNP antibodies of the IgM and IgG isotypes were detected in the serum and of the IgA isotype in the serum and gut secretions of sham immunized control mice. However, the administration of 30 micrograms of microencapsulated TNP-KLH in equal doses over 3 consecutive days resulted in the appearance of significant antigen-specific IgA antibodies over controls in the secretions, and of all isotypes in the serum by Day 14 after immunization (see last column of Table 1). These antibody levels were increased further on Day 28. In contrast, the oral administration of the same amount of unencapsulated antigen was ineffective at inducing specific antibodies of any isotype in any of the fluids tested.

H. Significance

These results are noteworthy in several respects. First, significant antigen-specific IgA antibodies are induced in the serum and mucosal secretions, a response which is poor or absent following the commonly used systemic immunization methods. Therefore, this immunization method would be expected to result in significantly enhanced immunity at the mucosa; the portal of entry or site of pathology for a number of bacterial and viral pathogens. Secondly, the microencapsulated antigen preparation was an effective immunogen when orally administered, while the microencapsulation resulted in a dramatic increase in efficacy, presumably due to targeting of and increased uptake by the Peyer's patch. Thirdly, the inductive phase of the immune response appears to be of long duration. While systemic immunization with protein antigens in the absence of adjuvants is characterized by peak in antibody levels in 7 to 14 days, the orally administered antigen-containing microcapsules induced responses were higher at Day 28 than Day 14. This indicates that bioerosion of the wall materials and release of the antigen is taking place over an extended period of time, and thus inducing a response of greater duration.

TABLE 1

THE INDUCTION OF TNP-SPECIFIC ANTIBODIES IN THE SERUM
AND MUCOSAL SECRETIONS OF BALB/C MICE BY ORAL
IMMUNIZATION WITH MICROENCAPSULATED TNP-KLH

| | | | ng Immunoglobulin/mL Sample | | | | | |
|---|---|---|---|---|---|---|---|---|
| | | | IgM | | IgG | | IgA | |
| Immunogen | Time After Immunization | Biologic Sample | Total | Anti-TNP | Total | Anti-TNP | Total | Anti-TNP |
| Control | Day 14 | Gut wash | <1 | <1 | 62 | <1 | 79,355 | 25 |
| | | Saliva | <40 | <10 | <40 | <10 | 2,651 | <10 |
| | | Serum | 445,121 | 6 | 5,503,726 | 37 | 1,470,553 | 32 |
| Unencapsulated TNP-KLH | Day 14 | Gut wash | 4 | 1 | 131 | <1 | 64,985 | 17 |
| | | Saliva | <40 | <10 | <40 | <10 | 1,354 | <10 |
| | | Serum | 298,733 | 11 | 6,000,203 | 29 | 1,321,986 | 21 |
| TNP-KLH Microcapsules | Day 14 | Gut wash | 3 | <1 | 130 | <1 | 95,368 | 222 |
| | | Saliva | <40 | <10 | <40 | <10 | 1,461 | 88 |
| | | Serum | 360,987 | 1,461 | 5,312,896 | 572 | 1,411,312 | 1,077 |
| Unencapsulated TNP-KLH | Day 28 | Gut wash | <1 | <1 | 94 | <1 | 88,661 | 64 |
| | | Saliva | <40 | <10 | <40 | <10 | 1,278 | <10 |
| | | Serum | 301,223 | 21 | 5,788,813 | 67 | 1,375,322 | 63 |
| TNP-KLH Microcapsules | Day 28 | Gut wash | 4 | <1 | 122 | 2 | 82,869 | 422 |
| | | Saliva | <40 | <10 | <40 | <10 | 1,628 | 130 |
| | | Serum | 320,192 | 1,904 | 5,951,503 | 2,219 | 1,277,505 | 1,198 |

III. BIOLOGICAL STUDY TWO

By far the largest mass of tissue with the capacity to function as an inductive site for secretory IgA responses is the Peyer's patches. These discrete nodules of lymphoreticular tissu are located along the entire length of the small intestine and appendix. The targeted delivery of intact antigen directly into this tissue to achieve high local concentration is currently believed to be the most effective means of inducing a disseminated mucosal IgA response. Recently acquired evidence supports the conclusion that biodegradable microcapsules represent an ideal vehicle to achieve this targeted vaccination

A. Uptake of Biocompatible and Biodegradable Microcapsules Into the Peyer's Patches Groups of mice were administered biodegradable microcapsules containing the fluorescent dye coumarin-6 as a suspension in tap water via a gastric tube. The microcapsule wall material chosen for these studies consisted of 85:15 poly(DL-lactide-co-glycolide) due to its ability to resist significant bioerosion for a period of six weeks. At various times from 1 to 35 days after administration, three representative Peyer's patches, the major mesenteric lymph nodes and the spleens from individual mice were removed, processed and serial frozen sections prepared.

When viewed with a fluorescence microscope using appropriate excitation and barrier filters the coumarin exhibited a deep green fluorescence which allowed the visual detection of microcapsules substantially less than 1 micrometer in diameter. All sections were viewed in order that the total number of microcapsules within each tissue or organ could be quantitated. The size of each internalized microcapsule was determined using a calibrated eyepiece micrometer and its location within the tissue or organ was noted. Internalized microcapsules of various sizes were observed in the Peyer's patches at 24 hours post oral administration and at all time points tested out to 35 days (Table 2). At no time were microcapsules of any size observed to penetrate into the tissue of the gut at any point other than the Peyer's patches. The total number of microcapsules within the Peyer's patches increased through Day 4 and then decreased over the following 31 days to approximately 15% of the peak number.

TABLE 2

Penetration and Persistence of Coumarin-6-Loaded 85:15 Poly(DL-Lactide-co-Glycolide) Microcapsules in the Peyer's Patches

| Time (days) | Total Number Observed | Proportion of Size (%) | | | Proportion at Location (%) | |
|---|---|---|---|---|---|---|
| | | Small <2 μm | Medium 2-5 μm | Large >5 μm | Dome | Deep |
| 1 | 296 | 47 | 35 | 18 | 92 | 8 |
| 2 | 325 | 45 | 32 | 23 | 83 | 17 |
| 4 | 352 | 46 | 31 | 23 | 76 | 24 |
| 7 | 196 | 21 | 29 | 41 | 88 | 11 |
| 14 | 148 | 16 | 29 | 55 | 98 | 2 |
| 21 | 91 | 7 | 27 | 66 | 98 | 2 |
| 28 | 63 | 5 | 24 | 71 | 100 | 0 |
| 35 | 52 | 6 | 19 | 79 | 97 | 3 |

This is consistent with the observation that free microcapsules could be observed on the surface of the gut villi at the 1, 2 and 4 day time points. It is of interest that approximately 10 hours following oral administration of the microcapsule suspension the coumarin-loaded microcapsules were frankly observable in the passed feces. This clearance was followed with the aid of an ultraviolet light source and by 24 hours the vast majority of the ingested microcapsules had been passed. Thus, the continued uptake of microcapsules into the Peyer's patches observed at 2 and 4 days must be attributed to th minor fraction of the input dose which became entrapped within mucus between the gut villi. In addition, efficiency of uptake for the entrapped microcapsules must be several orders of magnitude greater than that for the microcapsules present in the gut lumen, but above the mucus layer. These observations are important when these data are extrapolated to man; the tremendously larger mass of Peyer's patch tissue and the greatly increased transit time for the passage of material through the human small intestine relative to the mouse suggests that the efficiency of microcapsule uptake into the human Peyer's patches will be much higher.

Microcapsules of various sizes were observed within the Peyer's patches at all time points tested (Table 2). At the 1-, 2- and 4-day time points the proportion of <2 micrometers (45–47%), 2–5 micrometers (31–35%) and >5 micrometers (18–23%) microcapsules remained relatively constant. Evident at 7 days, and even more so at later time points, there was a shift in the size distribution such that the small (<2 micrometers) and medium (2-5 micrometers) microcapsules ceased to predominate and the large (>5 micrometers) microcapsules became the numerically greatest species observed. This shift was concurrent with the decrease in total microcapsule numbers in the Peyer's patches observed on and after Day 7. These results are consistent with the preferential migration of the small and medium sizes of microcapsules from the Peyer's patches while the large (>5 micrometers) microcapsules are preferentially retained.

Consistent with the preferential migration of the small and medium microcapsules out of the Peyer's patches are the data pertaining to the location of the microcapsules within the architecture of the Peyer's patches. When a microcapsule was observed within the Peyer's patch it was noted to be either relatively close to the dome epithelium where it entered the Peyer's patch (within 200 micrometers) or deeper within the lymphoid tissue (>200 micrometers from the closest identifiable dome epithelium) (Table 2). Microcapsules observed deep within the Peyer's patch tissue were almost exclusively of small and medium diameter. At 1 day post-administration 92% of the microcapsules were located close to the dome epithelium. The proportion of deeply located microcapsules increased through Day to 24% of the total and thereafter decreased with time to approximately 2% at Day 14 and later. Thus, the small and medium microcapsules migrate through and out of the Peyer's patches, while the large (>5 micrometers and <10 micrometers) microcapsules remain within the dome region for an extended period of time.

B. Microcapsule Migration to the Mesenteric Lymph Nodes and Spleen

A small number of microcapsules were observed in the mesenteric lymph nodes at 1 day post administration and the numbers progressively increased through Day 7 (Table 3). After Day 7 the numbers decreased, but were still detectable on Day 35. The size distribution clearly showed that microcapsules 5 micrometers in diameter did not enter this tissue and the higher proportion of small (<2 micrometers) relative to medium (2-5 micrometers) microcapsules at the earlier time points indicated that the smaller diameter microcapsules migrate to this tissue with greatest efficiency. In addition, at the earlier time points the majority of the microcapsules were located just under the capsule in the subcapsular sinus. Later time points showed a shift in the distribution to deep within the lymph node structure and by day 14 90% of the microcapsules were located within the cortex and medullary regions. The observation that the microcapsules are first detected in or near the subcapsular sinus is consistent with their entry into this tissue via the lymphatic which drain the Peyer's patches. A progressive increase in the proportion of the microcapsules located deep in this tissue, clearly discernable at Day 4, followed by a progressive drop in the total numbers on Day 14 and later suggests that the microcapsules progress through this tissue and extravasate the efferent lymphatic drainage.

TABLE 3

Migration of Coumarin-6-Loaded 85:15 Poly(DL-Lactide-co-Glycolide) Microcapsules Into and Through the Mesenteric Lymph Nodes

| Time (days) | Total Number Observed | Proportion of Size (%) | | | Proportion at Location % | |
|---|---|---|---|---|---|---|
| | | Small <2 μm | Medium 2-5 μm | Large >5 μm | Subcapsular Sinus | Deep |
| 1 | 8 | 50 | 50 | 0 | 100 | 0 |
| 2 | 83 | 76 | 24 | 0 | 95 | 5 |
| 4 | 97 | 73 | 27 | 0 | 73 | 27 |
| 7 | 120 | 67 | 32 | 0 | 64 | 36 |
| 14 | 54 | 83 | 17 | 0 | 9 | 91 |
| 21 | 20 | 75 | 25 | 0 | 5 | 95 |
| 28 | 15 | 67 | 32 | 0 | 0 | 100 |
| 35 | 9 | 44 | 56 | 0 | 0 | 100 |

Similar examination of the spleen showed that no microcapsules were detectable until Day 4 post-administration. Peak numbers of microcapsules were not observed in this organ until Day 14. As in the case of the mesenteric lymph nodes, no microcapsules of >5 micrometers diameter were observed. At all time points the microcapsules were observed deep in this organ within the cortex. It should be noted that the peak number of microcapsules was observed in the spleen at a time when the majority of the microcapsules present in the mesenteric lymph nodes was deeply located and the total numbers falling. These data are consistent with the known pattern of lymph drainage from the Peyer's patches to the mesenteric lymph nodes and from the mesenteric lymph nodes to the bloodstream via the thoracic duct. Thus, it appears that the microcapsules present in the spleen have traversed the Peyer's patches and mesenteric lymph nodes and have entered the spleen via the blood circulation.

A total of 9 microcapsule wall formulations have been tested and all have been found to enter the Peyer's patches and migrate through the lymphoid tissues of the body with similar kinetics and restrictions imposed by size. The wall materials chosen for these studies consisted of polymers that varied in water uptake, biodegradation, and hydrophobicity. These polymers included polystyrene, poly(L-lactide), poly(DL-lactide), poly(-hydroxybutyric acid), poly(methyl methacrylate), ethyl cellulose, cellulose acetate hydrogen phthalate, and cellulose triacetate. In addition, immunohistochemical studies have shown that the small and medium sizes of microcapsules which migrate through the body do so within phagocytic cells which bear the macrophage surface marker MAC-1.

C. Induction of a Serum Immune Response by Oral Immunization with Microencapsulated Vaccine Antigens The results presented in Section V below which show that (a) strong adjuvant activity is imparted by microencapsulation and (b) microcapsules <5 micrometers in diameter disseminate to the mesenteric lymph nodes and spleen after entering through the Peyer's patches, suggested that it would be feasible to induce a systemic immune response by oral immunization with vaccine incorporated into appropriately sized biodegradable microcapsules This possibility was confirmed in experiments in which groups of mice were immunized with 100 micrograms of Staphylococcal enterotoxoid B in soluble form or within microcapsules with a wall composition of 50:50 poly(DL-lactide-coglycolide). These mice were administered the soluble or microencapsulated toxoid via gastric tube on three occasions separated by 30 days, and plasma samples were obtained on Days 10 and 20 following each immunization. The data presented in Table 4 show the plasma end point titers of the IgM and IgG anti-toxin responses for the Day 20 time point after the primary, secondary and tertiary oral immunizations.

mL during collection. Although it is difficult to determine the exact dilution factor this imposes on the material collected, it is safe to assume that the IgA concentration is at minimum 10-fold higher in the mucus which bathes the gut, and this has not been taken into account in the measurements presented here.

These data clearly demonstrate the efficacy of microencapsulated enterotoxoid in the induction of a secre-

TABLE 4

Systemic Anti-Toxin Response Induced by Oral Immunization with Microencapsulated Versus Soluble Staphylococcal Enterotoxoid B

| Toxoid Dose μg Per Immunization | Form | Plasma Anti-Toxin Titer on Day 20 Following Oral Immunization | | | | | |
|---|---|---|---|---|---|---|---|
| | | Primary | | Secondary | | Tertiary | |
| | | IgM | IgG | IgM | IgG | IgM | IgG |
| 100 | Microencapsulated | 80 | 1,280 | 320 | 5,120 | 1,280 | 40,960 |
| 100 | Soluble | <20 | <20 | 80 | <20 | 640 | <20 |

Mice receiving the vaccine incorporated in microcapsules exhibited a steady rise in serum antibodies specific to the toxin with each immunization while soluble enterotoxoid was ineffective This experiment employed the same lot of microcapsules and was performed and assayed in parallel with the experiments presented in Tables 7, 8 and 9 below. Therefore, these data directly demonstrate that oral immunization with microencapsulated Staphylococcal enterotoxoid B is more effective at inducing a serum anti-toxin response than is the parenteral injection of the soluble enterotoxoid at its optimal dose. In a similar manner, i has also been shown that oral immunization with Type III pneumococcal polysaccharide in microcapsules is more effective at inducing a serum antibody response than the parenteral administration of an optimal dose of this vaccine.

tory Ig anti-toxin response in both the gut and at a distant mucosal site when administered orally. Furthermore, through the use of a mixture of microcapsules with a range of diameters from <1 to 10 micrometers it is possible to induce this mucosal response concomitantly with a strong circulating antibody response. This suggests that a variety of vaccines can be made both more effective and convenient to administer through the use of microencapsulation technology.

TABLE 5

Mucosal Anti-Toxin Response Induced by Oral Immunization with Microencapsulated Versus Soluble Staphylococcal Enterotoxoid B

| Toxoid Dose (μg) per Immunization | Form | IgA Anti-Toxin Titer Following Oral Immunization | | | |
|---|---|---|---|---|---|
| | | Day 10 | | Day 20 | |
| | | Saliva | Gut Wash | Saliva | Gut Wash |
| 100 | Microencapsulated | 1,280 | 1,024 | 640 | 256 |
| 100 | Soluble | <10 | <8 | <10 | <8 |

D. Induction of a Secretory IgA Response by Oral Immunization with Microencapsulated Vaccine Antigens The secretory IgA response was examined in the same group of mice which had been evaluated for the induction of systemic immunity through oral immunization (Section IV.C above). It was reasoned that the characteristics of this lot of enterotoxoid-containing microcapsules, a heterogeneous size range from <1 micrometer to approximately 10 micrometer, made it likely that a proportion of the microcapsules slowly released the toxoid while fixed in the Peyer's patches. Therefore, on Days 10 and 20 following the tertiary oral immunizations saliva and gut wash samples were obtained and assayed for toxin-specific antibodies o the IgA isotype. In contrast to the inability of the soluble toxoid to evoke a response when administered orally, the ingestio of an equal amount of the toxoid vaccine incorporated into microcapsules resulted in a substantial mucosal IgA anti-toxoid response in both the saliva and gut secretions. It should be pointed out that the gut secretions from each mouse are diluted into a total of 5

IV. BIOLOGICAL STUDY THREE

Absorption of Pharmaceuticals

The following example shows that small microcapsules (less than 5 micrometers, preferably 1 to 5 microns) can also improve the absorption of pharmaceuticals as well as antigens int the blood stream. Etretinate, (All-E)-9-(4-methoxy-2,3,6,-trimethyl) phenyl-3,7-dimethyl-2,4,8-nonatetraenoic acid, ethyl ester) was microencapsulated in 50:50 poly(DL-lactide-co-glycolide). The microcapsules were 0.5 to 4 micrometers in diameter and contained 37.2 wt % etretinate. These etretinate microcapsules as well as unencapsulated etretinate was administered to mice by oral lavage using wt % Tween 80 in water as a vehicle. Only single doses of 50 mg etretinate/kg were given. Blood from the dosed mice was collected at specified time intervals and the serum of this blood was quantified for etretinate and/or its metabolites using a high-performance chromatographic procedure. The results shown below show that mic treated with the etretinate microcapsules had significantly highe levels of etretinate than mice treated with unencapsulated etretinate. Like the less than 5-micrometers vaccine microcapsules, it is believed that the microcapsules carry the etretinate to the blood stream via the lymphoidal tissue (Peyer's patches) in the gastrointestinal tract. This same approach shoul be applicable to increasing the absorption of other drugs, where its application would be especially useful for the delivery of biological pharmaceuticals such as peptides, proteins, nucleic acids, and the like.

TABLE 6

Concentration of Etretinate in Mouse Serum After Oral Dosing With Microencapsulated and Uncapsulated Etretinate

| Times/hr | Etretinate Concentration, ng/mL | |
|---|---|---|
| | Microcapsules | Uncapsulated Drug |
| 1 | 4,569 | 191 |
| 3 | 634 | 158 |
| 6 | 242 | <31 |
| 24 | ND | ND |

ND = None detected

V. BIOLOGICAL STUDY FOUR

When one receives a vaccine by injection usually two to three or more administrations of the vaccine are required to illicit a good immune response in man or animals. Typically, the first injection is given to afford a primary response, the second injection is given to afford a secondary response, and a third injection is given to afford a tertiary response. Multiple injections are needed because repeated interaction of the antigen with immune system cells is required to stimulate a strong immunological response. After receiving the first injection of vaccine, a patient, therefore, must return to the physician on several occasions to receive the second, third, and subsequent injections to acquire protection. Often patients never return to the physician to get the subsequent injections.

The vaccine formulation (antigen) that is injected to a patient is the same as that used for the first and subsequent administrations, and usually consists of an antigen in associatio with an adjuvant. For instance, an antigen can be bound to alum. During the first injection, the use of the antigen/adjuvant combination is important so the immune system recognizes the presence of the antigen. The adjuvant aids in the recognition process by ensuring that the antigen remains in contact with immune system cells for a sufficient period of time to stimulate an immune response. During the second and third injections, the administration of the antigen improves the immune response of the body to the antigen. The second and third administrations or subsequent administrations, however, do not necessarily require the need of an adjuvant.

Alza Corporation has described methods for the continuous release of an antigen and an immunopotentiator (adjuvant) to stimulate an immune response (U.S. Pat. No. 4,455,142). This invention differs from the Alza patent in two important manners. First, no immunopotentiator is required to obtain an immune response, and second, the antigen is not continuously released from the delivery system.

The present invention concerns the formulation of vaccine (antigen) into microcapsules (or microspheres) whereby th antigen is encapsulated in biodegradable polymers, such as poly(DL-lactide-co-glycolide). More specifically, different vaccine microcapsules are fabricated and then mixed together such that a single injection of the vaccine-microcapsule mixture improves the primary immune response and automatically delivers antigen in a pulsatile fashion at later times to afford secondary tertiary, and subsequent responses.

The mixture of microcapsules consists of small and large microcapsules. The small microcapsules, less than 10 microns, preferably less than 5 micrometers, or more preferable 1 to 5 micrometers, improve the primary response (without the need of an adjuvant) because the small microcapsules are recognized and take up by macrophages. The microcapsules inside of the macrophages then release the antigen which is subsequently processed and presented on the surface of the macrophage to give the primary response. The larger microcapsules, greater than 5 micrometers, preferably greater than 10 microns, but not so large that they cannot be administered for instance by injection, preferably less than 250 micrometers, are made with different polymers so that as they biodegrade at different rates, they release antigen in a pulsatile fashion.

Using the present invention, the composition of the antigen microcapsules for the primary response is basically the same as the composition of the antigen microcapsules used for the secondary, tertiary, and subsequent responses. That is, the antigen is encapsulated with the same class of biodegradable polymers. The size and pulsatile release properties of the antigen microcapsules then maximizes the immune response to the antigen.

The preferred biodegradable polymers are those whose biodegradation rates can be varied merely by altering their monomer ratio, for example, poly(DL-lactide-co-glycolide), so that antigen microcapsules used for the secondary response will biodegrade faster than antigen microcapsules used for subsequent responses, affording pulsatile release of the antigen.

In summary, by controlling the size of the microcapsules of basically the same composition, one can maximize the immune response to an antigen. And also important is having small microcapsules (microcapsules less than 10 micrometers, preferably less than 5 micrometers, most preferably 1 to 5 micrometers) in the mixture of antigen microcapsules to maximize the primary response. The use of such small microcapsules becomes even more important when one attempts to illicit an immune response to less immunogenic compounds such as killed vaccines, subunit vaccines, low-molecular-weight vaccines such as peptides, and the like.

A. Adjuvant Effect Imparted by Microencapsulation

Research in our laboratories has shown that microencapsulation results in a profoundly heightened immune response to the incorporated antigen or vaccine in numerous experimental systems. An example is provided by the direct comparison of the level and isotype distribution of the circulating antibody response to Staphylococcal enterotoxin B, the causative agent of Staphylococcal food poisoning, following immunization with either soluble or microencapsuled enterotoxoid. Groups of mice were administered various doses of the toxoid vaccine incorporated in 50:50 poly(DL-lactide-co-glycolide) microcapsules, or in soluble form, by intraperitoneal injection. On Days 10 and 20 following immunization plasma samples were obtained and assayed for anti-toxin activity by end-point titration in isotype-specific immunoradiometric assays (Table 7). The optimal dose of soluble toxoid (25 micrograms) elicited a characteristically poor immune response to the toxin which was detected only in the IgM isotype. In contrast, the administratio of 25micrograms of toxoid incorporated within microcapsules induced not only an IgM response, but an IgG response which was detectable at a plasma dilution of 1/2,560 on Day 20 post immunization. In addition, larger doses of toxoid could be administered in microencapsulated form without decreasing the magnitude of the response, as is seen with the 50 micrograms dose of soluble toxoid. In fact, the measured release achieved with the microcapsules allows for 4-5 times the dose to be administered without causing high zone paralysis, resulting in substantially heightened immunity. This adjuvant activity is even more pronouned following secondary (Table 8) and tertiary immunizations (Table 9).

TABLE 7

Primary Anti-Toxin Response to Microencapsulated Versus Soluble Staphylococcal Enterotoxoid B

| Toxoid Dose (µg) | Form | Plasma Anti-Toxin Titer | | | |
|---|---|---|---|---|---|
| | | Day 10 | | Day 20 | |
| | | IgM | IgG | IgM | IgG |
| 100 | Microencapsulated | 1,280 | 320 | 1,280 | 10,240 |
| 50 | Microencapsulated | 640 | 320 | 1,280 | 5,120 |
| 25 | Microencapsulated | 320 | <20 | 640 | 2,560 |
| 50 | Soluble | <20 | <20 | <20 | <20 |
| 25 | Soluble | 320 | <20 | 160 | <20 |
| 12.5 | Soluble | 40 | <20 | <20 | <20 |

TABLE 8

Secondary Anti-Toxin Response to Microencapsulated Versus Soluble Staphylococcal Enterotoxoid B

| Toxoid Dose (µg) per Immunization | Form | Plasma Anti-Toxin Titer | | | |
|---|---|---|---|---|---|
| | | Day 10 | | Day 20 | |
| | | IgM | IgG | IgM | IgG |
| 100 | Microencapsulated | 320 | 163,840 | 160 | 81,920 |
| 50 | Microencapsulated | 640 | 81,920 | 640 | 163,840 |
| 25 | Microencapsulated | 2,560 | 40,960 | 640 | 81,920 |
| 50 | Soluble | 160 | <20 | 80 | <20 |
| 25 | Soluble | 320 | 160 | 160 | 320 |
| 12.5 | Soluble | 160 | 40 | 80 | 80 |

TABLE 9

Tertiary Anti-Toxin Response to Microencapsulated Versus Soluble Staphylococcal Enterotoxoid B

| Toxoid Dose (µg) per Immunization | Form | Plasma Anti-Toxin Titer | | | |
|---|---|---|---|---|---|
| | | Day 10 | | Day 20 | |
| | | IgM | IgG | IgM | IgG |
| 100 | Microencapsulated | 1,280 | 655,360 | 640 | 327,680 |
| 50 | Microencapsulated | 2,560 | 327,680 | 280 | 327,680 |
| 25 | Microencapsulated | 2,560 | 327,680 | 640 | 163,840 |
| 50 | Soluble | 640 | 1,280 | 640 | 640 |
| 25 | Soluble | 320 | 10,240 | 80 | 10,240 |
| 12.5 | Soluble | 160 | 1,280 | 40 | 1,280 |

The Day 20 IgG anti-toxin response following secondar immunization was 512-fold higher in mice receiving 50 micrograms of microencapsulated toxoid than in mice receiving the optimal dose of soluble toxoid. Further, tertiary immunization with the soluble toxoid at its optimal dose was required to raise an antibody response to the toxin which was equivalent to that observed following a single immunization with 100 micrograms of microencapsulated enterotoxoid. Adjuvant activity of equal magnitude has been documented to common laboratory protein antigens such as haptenated keyhole limpet hemocyanin and carbohydrate antigens such as the polysaccharide vaccine to Type 3 *Streptococcus pneumoniae.*

Available evidence suggests that the mechanism of immune enhancement is not simply the result of a depot effect. In order for the adjuvant effect to be observed the microcapsule carrier must be <10 micrometer in diameter, suggesting that uptake and processing by macrophages or other phagocytic accessory cells is responsible for this effect.

B. Immune Response Obtained From a Single Administration of Microencapsulated Antigen A Japanese Encephalitis virus vaccine (Biken) was studied. The virus used is a product of the Research Foundation for Microbial Diseases of Osaka University, Suita, Osaka, Japan. The manufacturer recommends a three dose immunization series consisting of two doses of vaccine administered one to two weeks apart followed by administration of a third dose of vaccine one month after the initial immunization series. We have compared th antiviral immune responses of mice immunized with a standard thre dose schedule of JE vaccine to the antiviral response of mice immunized with a single administration of JE vaccine consisting o one part unencapsulated vaccine and two parts encapsulated vaccine. The JE microcapsules were >10 micrometers. The results of immunizing mice with JE vaccine by these two methods were compared by measuring the serum antibody titers against JE vaccin detected through an ELISA assay. The ELISA assay measures the presence of serum antibodies with specificity for JE vaccine components, however, it does not measure the level of virus neutralizing antibody present in the serum. The virus neutralizing antibody activity was therefore measured by virus cytopathic effect (CPE) inhibition assays and virus plaque reduction assays. The results of those assays are presented here.

Four experimental groups consisting of (1) untreated control mice which received no immunization; (2) mice which received 3.0 mg of JE vaccine (unencapsulated) on Day 0; (3) mice which received 3.0 mg of JE vaccine (unencapsulated) on Days 0, 14 and 42 (standard schedule) and (4) mice which received 3.0 mg of JE vaccine (unencapsulated) and 6.0 mg of JE vaccine (encapsulated) on day 0 were studied. The untreated controls provide background virus neutralization titers against which immunized animals can be compared. The animals receiving a single 3.0 mg dose of JE vaccine on Day 0 provide background neutralization titers against which animals receiving unencapsulated vaccine in conjunction with encapsulated vaccine can be compared. This comparison provides evidence that the administration of encapsulated vaccine augments the immunization potential of a single 3.0 mg dose of unencapsulated vaccine. The animals receiving 3 doses of unencapsulated vaccine provide controls against which the encapsulated vaccine group can be compared so as to document the ability of a single dose of encapsulated vaccine to produce antiviral activity comparable to standard three dose immunization schedule.

Serum samples collected on Days 21, 49 and 77 from ten animals in each experimental group were tested for their ability to inhibit the cytopathic effects induced by a standard challenge (100 TCID50) of JE virus. The results of the CPE inhibition assays, expressed as the highest serum dilution capable of inhibiting 50% of the viral CPE, are presented in Table 10. As is shown, the untreated control animals (Group 1) had no significant serum virus neutralizing activity at any timepoint tested. Of the ten animals receiving a single 3.0 dose of JE vaccine on Day 0 (Group 2), one did not develop any detectable virus neutralizing antibody. Of the remaining nine mice, the highest titer achieved was 254 which occurred on Day 49. The geometric mean antiviral titer for this experimental group peaked on Day 49. Of the ten animals receiving a standard schedule of three vaccine doses (Group 3), eight had a decrease in antibody activity from Day 49 to Day 77. The geometric mean titer for this group decreased by greater than 50% from Day 49 to Day 77. All ten animals receiving encapsulated JE vaccine (Group 4) developed serum antiviral activity. The geometric mean titer for this group increased from Day 21 to Day 77. The average titer occurring on Day 49 in this group was significantly lower than that occurring in the 3 vaccine dose group (Group 3) ($p=0.006$); however, the titer continued to increase from Day 49 to Day 77 which is in contrast to the 3 vaccine dose group. There was no significant difference in the average titer for these two groups in the Day 77 samples ($p=0.75$) indicating that the encapsulated vaccine group achieved comparable serum antiviral titers at Day 77. Unlike the 3 vaccine dose group (Group 3), the animals receiving encapsulated vaccine (Group 4) continued to demonstrate increases in serum virus neutralizing activity throughout the timepoints examined. In contrast to the standard vaccine treatment group, mice receiving encapsulated JE vaccine had a two-fold increase in the average serum neutralizing titer from Day 49 to Day 77. The Day 21 average antiviral titer from mice receiving microencapsulated vaccine was not significantly different from th Day 21 average titer of mice receiving a single dose of JE vaccin on Day 0 ($p=0.12$); however, the Day 49 and Day 77 average titers were significantly different for the two groups ($p=0.03$ and $p=0.03$, respectively). These data indicate that serum virus neutralizing titers similar to those produced by standard vaccine administration can be achieved by administering a single dose of encapsulated JE vaccine. Although the antiviral titers achieved with the excipient formulation used in this study did not increase as rapidly as those achieved with the standard vaccine, the serum neutralizing antibody activity did reach titers which are comparable to those achieved with the standard three dose vaccine schedule.

To further corroborate these findings, pooled samples produced by mixing equal volumes of each serum sample were prepared for each experimental group. These samples were submitted to an independent laboratory for determination of antiviral activity. The samples were tested by plaque reduction assay against a standard challenge of JE virus. The results of these assays, presented in Table 11, substantiate the findings described above. Although the animals receiving encapsulated vaccine did not reach peak titers as rapidly as did the standard vaccine group, the encapsulated vaccine did induce comparable virus neutralizing antibody activity. Futhermore, the encapsulated vaccine maintained a higher antiviral titer over a longer period of time course than did the standard vaccine. Thes results further support the conclusion that a single administration of microencapsulated vaccine can produce results comparable to those achieved with a three dose schedule of standard vaccine.

TABLE 10

RESULTS OF CPE INHIBITION ASSAYS ON SERUM SAMPLES FROM THE JE VACCINE IMMUNIZATION STUDIES

| Animal | Dilution of serum capable of reducing virus-induced CPE by 50% on Day | | |
|---|---|---|---|
| | 21 | 49 | 77 |
| Group 1 = Untreated Controls | | | |
| GMT[a] | <10 | 11 | 11 |
| Average | <10 | 11 | 11 |
| Maximum | <10 | 16 | <20 |
| Minimum | <10 | <10 | <10 |
| Group 2 = 3.0 mg unencapsulated JE vaccine IP on Day 0 | | | |
| GMT | 44 | 73 | 50 |
| Average | 55 | 95 | 71 |
| Maximum | 127 | 254 | 160 |
| Minimum | <10 | 13 | <10 |
| Group 3 = 3.0 mg unencapsulated JE vaccine IP on Days 0, 14, and 42 | | | |
| GMT | 507 | 3,880 | 1,576 |
| Average | 939 | 5,363 | 2,951 |
| Maximum | 4,064 | >10,240 | >10,240 |
| Minimum | 160 | 806 | 254 |
| Group 4 = Prototype microcapsule system IP on Day 0 | | | |
| GMT | 77 | 718 | 1,341 |
| Average | 103 | 1,230 | 2,468 |
| Maximum | 320 | 5,120 | 10,240 |
| Minimum | 13 | 160 | 254 |

[a]GMT = Geometric mean titers.

TABLE 11

RESULTS OF PLAQUE-REDUCTION ASSAYS ON POOLED SERUM SAMPLES FROM JE VACCINE IMMUNIZATION STUDIES

| Group | Treatment | Day | Serum dilution to reach | |
|---|---|---|---|---|
| | | | 50% endpoint | 80% endpoint |
| 1[a] | Controls | 0 | <10 | <10 |
| 1 | Controls | 14 | <10 | <10 |
| 1 | Controls | 21 | <10 | <10 |
| 1 | Controls | 42 | <10 | <10 |
| 1 | Controls | 49 | <10 | <10 |
| 1 | Controls | 84 | <10 | <10 |
| 2[b] | Unencapsulated JE | 0 | <10 | <10 |
| 2 | Unencapsulated JE | 14 | 160 | 20 |
| 2 | Unencapsulated JE | 21 | ND[c] | ND |
| 2 | Unencapsulated JE | 42 | 320 | 80 |
| 2 | Unencapsulated JE | 49 | 320 | 40 |
| 2 | Unencapsulated JE | 84 | 640 | 160 |
| 3[d] | Unencapsulated JE | 0 | <10 | <10 |
| 3 | Unencapsulated JE | 14 | 160 | 40 |
| 3 | Unencapsulated JE | 21 | 2,560 | 640 |
| 3 | Unencapsulated JE | 42 | 1,280 | 640 |
| 3 | Unencapsulated JE | 49 | 5,120 | 2,560 |
| 3 | Unencapsulated JE | 84 | 2,560 | 1,280 |
| 4[e] | Microencapsulated JE | 0 | <10 | <10 |
| 4 | Microencapsulated JE | 14 | 160 | 20 |
| 4 | Microencapsulated JE | 21 | 320 | 80 |
| 4 | Microencapsulated JE | 42 | 5,120 | 640 |
| 4 | Microencapsulated JE | 49 | 5,120 | 640 |
| 4 | Microencapsulated JE | 84 | 10,000 | 2,560 |

[a]Untreated controls.
[b]Animals received 3.0 mg of unencapsulated JE vaccine IP on Day 0.
[c]ND = Not determined (insufficient sample quantity).
[d]Animals received 3.0 mg of unencapsulated JE vaccine IP on Day 0, 14, and 42.
[e]Animals received 3.0 mg of unencapsulated and 6.0 mg of microencapsulated JE vaccine IP on Day 0.

It should be apparent, therefore, that there exists a number of possible approaches to vaccination by the injectable microcapsules of the present invention. Among these include multiple injections of small microcapsules, preferably 1 to 5 micrometers, that will be engulfed by macrophages and obviate the need for immunopotentiators, as well as mixtures of free antigen for a primary response in combination with microcapsulated antigen in the form of microcapsules having a diameter of 10 micrometers or greater that release the antigen pulsatily to potentiate secondary and tertiary responses and provide immunization with a single administration. Also, a combination or small microcapsules for a primary response and larger microcapsules for secondary and later responses may be used, thereby obviating the need for both immunopotentiators and multiple injections.

What is claimed is:

1. A method of potentiating the immune response of an animal, comprising the step of parenterally administering to said animal a mixture of effective amounts of first biocompatible microcapsules having a size between approximately 1 micrometer and approximately 10 micrometers and containing a bioactive agent adn second biocompatible microcapsules containing a bioactive agent, said first microcapsules providing a primary immunological response and said second microcapsules releasing said agent contained in said second microcapsules ina pulsed manner to potentiate a subsequent immunological response, wherein said bioactive agent is selected from the group consisting of an antigen and an allergen.

2. The method of claim 1, wherein said second biocompatible microcapsules have a size greater than 10 micrometers.

UNITED STATES PATENT AND TRADEMARK OFFICE
CERTIFICATE OF CORRECTION

PATENT NO. : 5,075,109
DATED : December 24, 1991
INVENTOR(S) : THOMAS R. TICE ET AL.

It is certified that error appears in the above-indentified patent and that said Letters Patent is hereby corrected as shown below:

Cover page, Item [75], Inventors, delete "Melinda G. Hollingshead; William M. Shannon".

Signed and Sealed this

Eleventh Day of April, 1995

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,075,109
DATED : December 24, 1991
INVENTOR(S) : Thomas R. Tice, et al.

It is certified that error appears in the above-identified patent and that said Letters Patent is hereby corrected as shown below:

In column 1, after line 7, insert a new paragraph to read

-- This invention was made with government support under Contract Number DAND17-86-C-6162 awarded by the Department of the Army of the United States Government. The U.S. Government has certain non-commercial rights in the invention. The U.S. Government does not have rights in the invention pertaining to drug delivery.--

Signed and Sealed this

Third Day of March, 1998

Attest:

BRUCE LEHMAN

Attesting Officer

Commissioner of Patents and Trademarks